United States Patent [19]
Alicot et al.

[11] 4,252,942
[45] Feb. 24, 1981

[54] PROCESS FOR THE PREPARATION OF THE BENZOTHIAZOLE-SULFENAMIDES

[75] Inventors: Michel Alicot, La Barthe de Neste; Laurent Ciccotto, Lannemezan; Adrien Tignol, Montrejeau, all of France

[73] Assignee: Produits Chimiques Ugine Kuhlmann, Courbevoie, France

[21] Appl. No.: 82,206

[22] Filed: Oct. 5, 1979

[30] Foreign Application Priority Data

Oct. 24, 1978 [FR] France ............................. 78 30143

[51] Int. Cl.³ .................. C07D 417/12; C07D 277/80
[52] U.S. Cl. ..................................... 544/135; 546/198; 548/161; 548/167; 548/168
[58] Field of Search ........................ 544/135; 546/198; 548/161, 167, 168

[56] References Cited

U.S. PATENT DOCUMENTS

| | | | |
|---|---|---|---|
| 2,840,556 | 6/1958 | Kinstler | 544/135 |
| 3,658,808 | 4/1972 | Kinstler | 548/167 |

FOREIGN PATENT DOCUMENTS 2056748  4/1971  France .

OTHER PUBLICATIONS

Carr et al., *J. Org. Chem.*, vol. 14, (1949), pp. 921-934.

*Primary Examiner*—Henry R. Jiles
*Assistant Examiner*—R. W. Ramsuer
*Attorney, Agent, or Firm*—Beveridge, DeGrandi, Kline & Lunsford

[57] ABSTRACT

A process for the preparation of benzothiazole-sulfenamides in which a benzothiazyl disulfide is reacted with a mixture comprising an amine halogenhydrate and an N-halogen amine derivative.

6 Claims, No Drawings

PROCESS FOR THE PREPARATION OF THE BENZOTHIAZOLE-SULFENAMIDES

The present invention relates to a new process for the preparation of the 2-benzothiazole-sulfenamides corresponding to the general formula:

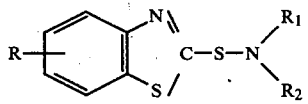
(I)

in which R represents a hydrogen atom, an alkyl group containing from 1 to 4 carbon atoms or a nitro group; $R_1$ represents a hydrogen atom, a straight or branched chain alkyl group containing from 1 to 8 carbon atoms, a cycloalkyl group containing from 5 to 7 carbon atoms or said cycloalkyl group substituted by an alkyl group containing from 1 to 2 carbon atoms (i.e. an alkylcycloalkyl group) or a cyanoalkyl group containing 3 carbon atoms; or a hydroxyalkyl group containing 2 carbon atoms; and $R_2$ represents a straight or branched chain alkyl group containing from 1 to 8 carbon atoms, a cycloalkyl group containing from 5 to 7 carbon atoms or said cycloalkyl group substituted by an alkyl group containing from 1 to 2 carbon atoms, a cyanoalkyl group containing 3 carbon atoms; or a hydroxyalkyl group containing 2 carbon atoms; or $R_1$ and $R_2$ represent alkylene groups containing from 4 to 6 carbon atoms connected by a simple bond or a heteroatom. As examples of such groups may be mentioned the piperidyl and morpholine rings.

The known processes relating to the preparation of the compounds of general formula (I) used as the original starting material, either mercaptobenzothiazole or benzothiazole disulfide.

In the first case, the following reactions are principally mentioned.

Oxidizing condensation of mercaptobenzothiazole with an amine in alkaline medium, generally in aqueous medium. The oxidizing agent is preferably chosen from sodium hypochlorite, hydrogen peroxide, chlorine or an alkaline persulfate. Examples of this process are given in French Pat. No. 852,118 filed Mar. 25, 1939 and U.S. Pat. No. 2,807,620 filed Dec. 22, 1955.

Condensation of the mercaptobenzothiazole salt with an N-halogen derivative of an amine. This process is proposed by French Pat. No. 1,165,505 filed Nov. 14, 1956, corresponding to U.S. Pat. No. 2,776,297, and U.S. Pat. No. 2,730,526 filed May 21, 1951.

In the case where the benzothiazole disulfide is the original starting material, an oxidizing condensation in the presence of an amine can also be used (French Pat. No. 852,118, supra). In a general manner, however, the known processes use the reaction of benzothiazole disulfide with an amine and its N-halogen derivative. U.S. Pat. No. 2,730,527 filed Dec. 12, 1952, No. 2,782,202 filed Feb. 19, 1957, and No. 3,022,300 filed Sept. 23, 1954, and British Pat. No. 856,421 filed May 27, 1957, are illustrations of processes elaborated according to this principle.

These different processes are not without disadvantages: the yields are sometimes insufficient; the quality of the products obtained cannot be entirely satisfactory (in particular for numerous applications, the content of benzothiazole disulfide may be very small). In addition these processes are often specific to a given product and do not allow to be obtained, for example, an equal result with a primary amine or a secondary amine. Some of them are exclusive to one or other of these two classes of amines.

Finally, a difficult problem to solve is that posed by the rejected material, which may be of a high volume and of which the chemical demand for oxygen can be very great; this is the case in particular with processes in aqueous medium carrying out the oxidizing condensation of mercaptobenzothiazole and an amine, in which a considerable excess of oxidizing agent is often necessary.

The process according to the present invention enables these disadvantages to be mitigated. In said process a benzothiazole disulfide of the general formula:

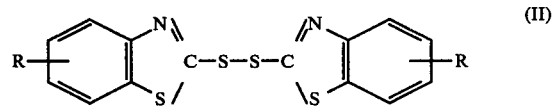
(II)

in which R has the same significance as above, is reacted with a mixture of amine halogenhydrate and an N-halogen amine of the general formula:

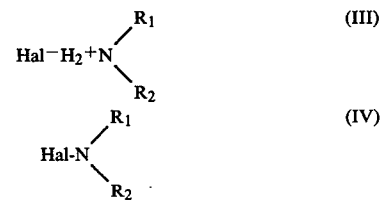

in which $R_1$ and $R_2$ have the same significance as above.

For one mole of benzothiazole disulfide there is used at least one mole of amine in the form of the N-halogen derivative and at least one mole of amine in the form of the halogenhydrate. Preferably a small excess of 0 to 5% is allowed of an amine equivalent with respect to the benzothiazole disulfide. It is however possible to use a larger excess, when in particular the recovery of the excess amine may be effected without difficulty.

The N-halogen amine and the amine halogenhydrate are used in a stoichiometric ratio.

The reaction is effected in a solvent medium miscible with water, preferably selected from the class of aliphatic alcohols, with a straight of branched chain, such as methyl, ethyl or isopropyl alcohols.

The operation is carried out in the presence of an alkaline agent capable of picking up the halogenated acid formed; it is preferably selected from the alkaline salts of carbonic acid or the hydroxides of the alkali or alkaline earth metals. An excess of an alkaline agent is not prejudicial.

The reaction is effected in a temperature range between 20° C. and the boiling temperature of the selected solvent, preferably between 40° C. and 70° C.

Although the process of the invention could be carried out by allowing in the reaction medium a content of water of the order of 10% by volume, it is preferable not to exceed the quantity of water produced by the reaction of neutralization of the halogen acid by the alkaline agent used.

The 2-benzothiazole-sulfenamide, solubilized in the reaction medium in proportion to its formation, is precipitated, after eventual filtration of the alkaline halide by-product, by addition of water; it is isolated by any known means, e.g. filtration, draining, etc.

The solvent, separated from the water formed during the reaction and the water of dilution, is able to be recycled. The water, in most cases on account of the high yields obtained, is also totally or partially able to be recycled.

The mixture of the N-halogen derivative and the primary or secondary amine halogenhydrate is first prepared by the action of a halogen on the corresponding amine, in the same solvent medium as that used for the synthesis of the 2-benzothiazole sulfenamide. The reaction may be represented as follows:

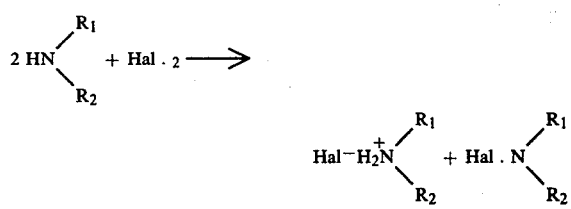

The measure of the potential of the reaction medium enables the rate of conversion of the amine to be easily controlled and the reaction of N-halogenation to be controlled in safety, by then avoiding in the case of the primary amines the formation of N-halogen derivatives which are thermally unstable and capable ultimately of decomposing in an explosive manner.

The halogenation reaction is effected at low temperature, preferably in the range of temperature from $-5°$ C. to $+10°$ C. so as to avoid the risks of dehydrohalogenation. It may be carried out continuously or discontinuously.

The following examples illustrate the invention without it being limited thereto.

EXAMPLE 1

(a) Preparation of the mixture of morpholine hydrochloride and N-chloro-morpholine.

In a 750 ml capacity reactor, fitted with an agitating device, a temperature indicator, a device for the introduction of gas, a pair of glass-methyl alcohol and Hg-Hg$_2$Cl$_2$-methyl alcohol electrodes and an output device in the immediate neighborhood of the electrodes, there are introduced for 45 minutes methyl alcohol and morpholine at the respective rates of 475 ml/hour and 122 g/hour, then, for 45 minutes chlorine at the rate of about 54 g/hour, until the value of the potential recorded between the two electrodes is $+100$ mv ($\pm 10$ mv). The temperature, during the introduction of the chlorine, is regulated at 0° C. to $+5°$ C.

After having formed an initial volume of mixture, it is followed by:

(b) Continuous preparation of the mixture by proceeding simultaneously with the following operations:

1. Introduction of methyl alcohol, morpholine and chlorine, at the respective rates of 475 ml/hour, 122 g/hour and 54 g/hour; the temperature is regulated at 0° C. to $+5°$ C. and the rate of chlorine feed is contingently adjusted so that the value of the potential is $+100$ mv ($\pm 10$ mv); and 2. Removal of the reaction product at a rate such that the volume in the reactor is kept constant.

The solution is stored in a tank maintained at 0° C. to $+5°$ C. or is used directly in the following phase of the process.

(c) Synthesis of the N-(2-benzothiazole-sulfenyl)-morpholine.

700 ml of methyl alcohol, 332 g of benzothiazyl disulfide (1 mole) and 120 g of sodium carbonate are charged with agitation into a reactor of 2000 ml capacity fitted with an agitating device and a temperature regulator.

The mixture is heated to 50° C.–55° C. and there is introduced, while maintaining the agitation and in about 15 minutes, 975 ml of the mixture prepared according to (a) above containing 127.6 g of N-chloro-morpholine (i.e. 1.05 mole) and 129.6 g of morpholine hydrochloride (i.e. 1.05 mole).

The reaction, slightly exothermic, is regulated at 50° C. to 55° C. After one and a half hours, the precipitate of sodium chloride formed is filtered off and washed three (3) times with 50 ml to 100 ml of methyl alcohol each time.

The whole of the filtrate and the alcohol washings is cooled with agitation at $+15°$ C. The N-(2-benzothiazyl-sulfenyl)-morpholine is partially precipitated. 2000 ml of cold water (between 10° C. and 15° C.) are added and the product is maintained with vigorous agitation for 1½ to 2 hours. The sulfenamide is completely insolubilized. It is filtered off, washed three times with about 250 ml of water each time, drained and dried at a temperature less than 40° C. to 45° C. 502 g of N-(2-benzothiazyl-sulfenyl)-morpholine are obtained of melting point (uncorrected) of 85°–86° C. with a content of benzothiazyl disulfide of less than 0.2%. The yield, calculated with respect to the benzothiazyl disulfide, is 99.55%.

From the filtration mother liquors, and by distillation, recyclable methyl alcohol is recovered.

If there are used two similar installations of suitable capacity working alternately to produce the sulfenamide (c) the continuous production of the mixture (b) enables the whole process to be made pseudo-continuous.

EXAMPLE 2

(a) Preparation of the mixture of cyclohexylamine hydrochloride and N-monochloro-cyclohexylamine.

900 ml of methyl alcohol and 200 g of cyclohexylamine (i.e. 2.10 moles) are introduced into a reactor of 1500 ml capacity, provided with an agitation device, a temperature recorder, a gas intake, a pair of glass-methyl alcohol and Hg-Hg$_2$Cl$_2$-methyl alcohol electrodes, and a withdrawal outlet in the immediate neighborhood of the electrodes. While maintaining the temperature at 0° C. to $+5°$ C., gaseous chlorine is added until the value of the potential recorded between the two electrodes is equal to $-100$ mv ($\pm 10$ mv). The introduction of the chlorine lasts about one hour and fifteen minutes and 80 g thereof are consumed. The solution obtained is maintained at 0° C. to $+5°$ C.

(b) Synthesis of N-(2-benzothiazyl-sulfenyl)-cyclohexylamine.

Into a 5000 ml reactor provided with an agitation device and a temperature recorder, 800 ml of methyl alcohol, 332 g of benzothiazyl disulfide (i.e. 1 mole) and 84 g of calcium hydroxide are introduced, and the mixture is heated to 40° C.

The whole of the solution prepared in (a), containing 140.2 g of N-monochlorocyclohexylamine and 142.3 g of cyclohexylamine hydrochloride (i.e. 1.05 moles of each of these two constituents) is added with agitation, in a period of about 15 minutes.

The reaction, slightly exothermic, is regulated to +40° C. After 4 hours contact, it is cooled, always with agitation, to a temperature of +10° C. to +15° C. and 2000 ml of cold water (+15° C.) are added. The N-(2-benzothiazyl-sulfenyl)cyclohexylamine is completely precipitated after two hours agitation at the temperature of +15° C.; it is then filtered, washed with about 150 ml of water 4 to 5 times (until the chloride ions are eliminated) and drained. After drying at a temperature less than 40° C. to 45° C., 486 g of sulfenamide are obtained, of melting point (uncorrected) 98° C. to 101° C., having a content of benzothiazyl disulfide of less than 0.4%. The yield calculated with respect to the benzothiazyl disulfide is 92%.

EXAMPLE 3

(a) Preparation of the mixture of tertiary-butylamine hydrochloride and N-chloro-tertiary-butylamine.

900 ml of methyl alcohol and 102.5 g of tertio-butylamine (i.e. 2.5 moles) are introduced into a reactor of 5000 ml capacity, provided with an agitation device, a temperature recording device, a gas intake, a pair of glass-methyl alcohol and $Hg-Hg_2Cl_2$-methyl alcohol electrodes and an outlet in the immediate neighborhood of the electrodes. While maintaining the temperature at between 0° C. and +5° C., gaseous chlorine is introduced until the value of the potential between the two electrodes is equal to +10 mv (±10 mv). 98 g of chlorine are thus absorbed in an hour.

(b) Synthesis of the N-(2-benzothiazyl-sulfenyl)-t-butylamine.

332.5 g of benzothiazyl disulfide (i.e. one mole) and 144 g of sodium carbonate are suspended in 500 ml of methyl alcohol in an attached reactor of 5000 ml capacity fitted with an agitating device and a temperature recorder.

The solution prepared in (a) containing 134 g of N-monochloro-t.butylamine and 136.5 g of t.butylamine hydrochloride is added, always with agitation, and in about 20 minutes. The mixture is heated at 60°-65° C. for one hour. After cooling to 10°-15° C., 1500 ml of water are added and agitation is effected for three hours at 15°-20° C. The precipitated sulfenamide is filtered off, washed with water until the chloride ions are eliminated, drained and dried at a temperature below 40°-45° C.

453 g of sulfenamine are obtained of melting point (uncorrected) of 107° C. and of which the content of benzothiazyl disulfide is less than 0.4%. The yield with respect to the benzothiazyl disulfide is 95%.

What is claimed is:

1. A process for the preparation of benzothiazyl-sulfenamides of the formula:

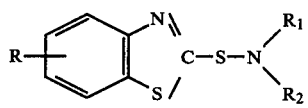

in which R represents hydrogen, alkyl or nitro; represents hydrogen, straight or branched chain al cycloaklyl, alkylcycloalkyl, cyanoalkyl or hydroxkyl, $R_2$ represents straight or branched chain al cycloalkyl, alkylcycloalkyl, cyanoalkyl or hydroxkyl or $R_1$ and $R_2$ represent alkylene connected t simple or a heteroatom linkage, in which a benzothi: disulfide of the formula:

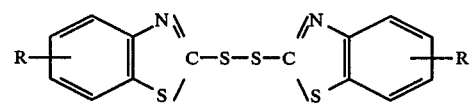

is reacted in the presence of an alkaline agent wit mixture comprising an amine halogenhydrate of formula:

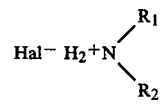

and an N-halogen amine of the formula:

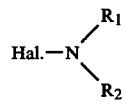

R, $R_1$ and $R_2$ having the same significance as in form (I).

2. The process according to claim 1 in which at le one mole of halogenhydrate and at least one mole N-halogen amine are used to one mole of disulfide.

3. The process according to claim 1 in which halogenhydrate and the N-halogen amine are in st chiometric proportion.

4. The process according to claim 1 or 3 in which mixture of halogenhydrate and N-halogen amine is p pared in advance by the action of the halogen $Hal._2$ an amine of the formula:

in the same solvent which was used for the synthesis the sulfenamide, the temperature being preferably l than 10° C.

5. The process according to claim 1 in which ι reaction is effected in a solvent miscible with water 6. The process according to claim 1 or 5 in which ι reaction is effected at between 20° C. and the boili temperature of the solvent.

* * * * *